US006623271B2

United States Patent
Pruden

(10) Patent No.: US 6,623,271 B2
(45) Date of Patent: Sep. 23, 2003

(54) MOUTH SIMULATOR APPARATUS

(75) Inventor: Jana N. Pruden, BelleMead, NJ (US)

(73) Assignee: Jeneric/Pentron Incorporated, Wallingford, CT (US)

( * ) Notice: Subject to any disclaimer, the term of this patent is extended or adjusted under 35 U.S.C. 154(b) by 0 days.

(21) Appl. No.: 09/861,152

(22) Filed: May 18, 2001

(65) Prior Publication Data

US 2002/0006598 A1 Jan. 17, 2002

Related U.S. Application Data

(60) Provisional application No. 60/205,663, filed on May 19, 2000.

(51) Int. Cl.$^7$ ............................................. A61C 19/10
(52) U.S. Cl. .................................................. 433/26
(58) Field of Search ..................... 433/26, 229, 77, 433/34, 213

(56) References Cited

U.S. PATENT DOCUMENTS

| | | | | |
|---|---|---|---|---|
| 1,938,222 A | * | 12/1933 | Green | 433/26 |
| 2,412,352 A | * | 12/1946 | Myerson | 433/26 |
| 2,760,269 A | | 8/1956 | Adams | |
| 3,436,156 A | * | 4/1969 | Adler et al. | 356/423 |
| 5,725,372 A | * | 3/1998 | Leon | 433/26 |
| 5,989,022 A | * | 11/1999 | Yamamoto et al. | 433/26 |
| 6,030,209 A | | 2/2000 | Panzera et al. | 433/26 |
| 2002/0015933 A1 | | 2/2002 | Berner | 433/26 |

OTHER PUBLICATIONS

Dentsply International, Inc., The Truflex Selection Rim product brochure. Form No. 2360, 4–77.

* cited by examiner

Primary Examiner—Kevin Shaver
Assistant Examiner—Melba Bumgarner
(74) Attorney, Agent, or Firm—Ann M. Knab

(57) ABSTRACT

A mouth simulator apparatus that simulates the atmosphere of the oral environment so that a dental restorative material can be viewed after manufacture and prior to insertion in the patient's mouth. One is able to view the dental restorative material in comparison to shade guide components under the same lighting conditions as present in the oral cavity.

4 Claims, 3 Drawing Sheets

MOUTH SIMULATOR APPARATUS

This application claims benefit to U.S. provisional application serial No. 60/205,663, filed May 19, 2000.

FIELD OF THE INVENTION

The present invention relates generally to dental porcelain restorations and methods of manufacture thereof. In particular, this invention relates to a mouth simulator apparatus and method of use of the apparatus for accurately matching the color of a porcelain or composite restoration to a patient's natural tooth color and/or to shade guide components.

BACKGROUND OF THE INVENTION

In the restoration of a tooth or a set of teeth, the tooth color must be correctly selected. A tooth restoration should not only fit harmoniously into the arc of the teeth but it should also be adapted to the individual conditions of the adjacent teeth and the entire set of teeth and the oral soft tissue in its influence of colors.

Viewing the color of a finished restoration with respect to the color of teeth in a patient's mouth to determine and evaluate whether the restoration closely matches the teeth in a patient's mouth is subjective and can often be difficult. The existence of controlled and uncontrolled variables such as light sources, dissimilar geometries and dimensions, angles of view, and background and surrounding influences further complicate the process. Traditionally, restorations have been viewed by holding the restoration in one's hand and using the flesh tones of one's hand to simulate gum tissue. Viewing the restorations in this way does not create a very effective environment due to the aforementioned variables and influences present. It would be advantageous to view the restorations in an environment that provides the same light, effects and influences existing in one's mouth.

More recent trends in the dental industry have involved spectrophotometer technology whereby a spectral camera is used to read the shades of teeth and restorations and thereby provide data which allows one to produce a restoration with dental materials having a shade which corresponds to the shade measured and received by the spectral camera. Even with the advent of spectrophotometer technology, there remains a need for the human eye to view the finished restoration in a virtual or simulated environment of one's mouth to provide a restoration that looks as natural as possible.

It would be advantageous to reduce the subjectivity involved in determining the hue, chroma, value and translucency data. It would be beneficial to reduce the subjectivity involved in viewing finished restorations. There is a need to provide an effective environment to compare spectrophotometric readings of ceramic and composite crowns and shade guides with spectral data of intraoral spectrophotometric recordings of natural teeth.

SUMMARY OF THE INVENTION

These and other objects and advantages are accomplished by the mouth simulator apparatus of the present invention that simulates the atmosphere of the oral environment so that a dental restorative material can be viewed after manufacture and prior to insertion in the patient's mouth. One is able to view the dental restorative material under the same lighting conditions as present in the oral cavity. The jaw bone in the oral cavity is represented by a dental arch in the mouth simulator apparatus. Pink-colored oral tissue material in the form of putty is placed on the dental arch and is somewhat soft, flexible and adaptable for embedding different-sized and -shaped dental restorations and various shade guides for shade comparison to the dental restorations.

The apparatus may be positioned in an enclosure such as in a three-sided box or similar enclosure with a dark or black interior. This reduces or blocks any light radiating from behind the apparatus, to further simulate the oral cavity since the back of one's mouth is dark.

BRIEF DESCRIPTION OF THE DRAWINGS

Features of the present invention are disclosed in the accompanying drawings, wherein similar reference characters denote similar elements throughout the several views, and wherein.

DESCRIPTION OF THE INVENTION

Figure 1:
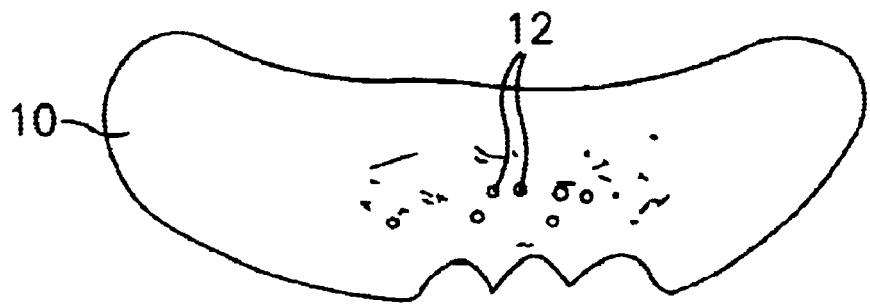
FIG. 1 is an elevational view of the dental arch of the mouth simulator apparatus herein.

The invention is directed to a mouth simulator apparatus comprising a hard, matrix material contoured in the shape of the anterior dental arch. The matrix material may include any polymeric or resinous material such as thermoplastic and thermosetting materials which are relatively rigid when cured. Examples of such materials include but are not limited to polyethylene, polypropylene, polyamides, polyester, polyolefins, polyimides, polyarylates, polyurethanes, vinyl esters or epoxy-based materials, styrenes, styrene acrylonitriles, ABS polymers, polysulfones, polyacetals, polycarbonates, polyphenylene sulfides, polyarylsulfides, acrylonitrile-butadiene-styrene copolymers, polyurethane dimethacrylates (hereinafter abbreviated to PUDMA), and the like. It is preferable that the matrix material is a pink color to simulate the environment of one's mouth.

On top of the hard dental arch is placed soft pink tissue colored "putty" that remains somewhat soft, flexible and adaptable for embedding different-sized and -shaped restorations and shade guides. The putty will adhere adhesively to the dental arch and permit temporary attachment of restorative materials and teeth. The putty material may be any of several pink and brown tissue tints to simulate different oral environments and may include, but is not limited to any soft putty-like material such as wax, silicone, polyurethane, soft rubber and the like. Reference is hereby made to U.S. Pat. No. 2,760,269, to Adams et al., which shows an artificial teeth selection rim and which patent is herein incorporated by reference.

As stated above, the putty is soft and malleable to allow for temporary insertion of crowns or other dental restoratives thereon. A crown will be used as the example to describe the invention herein although other dental restoratives may also be inserted in the mouth simulator apparatus to determine the correct shade. The mouth simulator apparatus is useful to view a crown to determine whether the shade is appropriate. After a crown has been fabricated, it is inserted into the putty section of the apparatus. Shade guide components or denture teeth are inserted on each side of the crown for comparison thereto to determine if the crown appropriately matches the shade of the shade guide components or denture teeth. The mouth simulator apparatus provides an environment similar to that of the patient's mouth for viewing the newly fabricated crown, providing color, lighting and background found inside the oral environment which is much different from open environmental factors. By viewing the crown in the mouth simulator apparatus, the dental technician can determine whether the restoration matches the shade desired and if changes are necessary, the technician may readily alter the shade and color to appropriately match the desired shade. By doing so, an esthetically pleasing and accurately matching restoration is provided. Modifications to the restorations are made prior to sending to the dentist, whom would otherwise have to view the restoration inside the patient's mouth, and determine whether the match is appropriate. This would involve sending the restoration back to the technician for modifications and would otherwise increase the time, labor and money involved in obtaining an appropriate restoration. According to the invention herein, unnecessary time, labor and money is avoided.

In order to further replicate the environment of a patient's mouth, the apparatus may be positioned in an enclosure such as in a three-sided box or similar enclosure with a dark or black interior or set against a dark or black background such as a cloth or a board situated behind and/or around the apparatus, or a replica of a human head. This reduces or blocks any light radiating from behind the apparatus, to further simulate the oral cavity since the back of one's mouth is dark. Reference is hereby made to commonly assigned U.S. Pat. No. 6,030,209 entitled "Method for Accurately Preparing the Color of a Dental Restoration" which is herein incorporated by reference.

Depending upon the type of restoration, i.e., all ceramic, porcelain-fused-to-metal, or polymeric composite restorations, material may be added to the interior of the restoration to further simulate the environment of one's mouth, since the restorations are being viewed without any tooth material or stump underneath the restoration. For all ceramic and composite restorations, it may be necessary to insert some composite or similar material inside the restorations temporarily, to provide some understructure and depth thereto to simulate the tooth structure to which it will be finally attached.

In order to view the restoration in the mouth simulator apparatus, it is necessary to have denture teeth or shade guide components to accurately compare the restoration to the appropriate shade prescribed. The mouth simulator apparatus can be provided in a kit form which may include a variety of pink and brown shaded putty materials to closely match the shade of a patient's gum. Also included in the kit may be a variety of denture teeth in various shades of porcelain and/or composite materials used in the dental industry. Alternatively, the technician may use shade guide components available from commercial shade guide systems or custom-designed shade guide components, which can be temporarily adhered to the putty material on one or both sides of the restoration.

Figure 2:
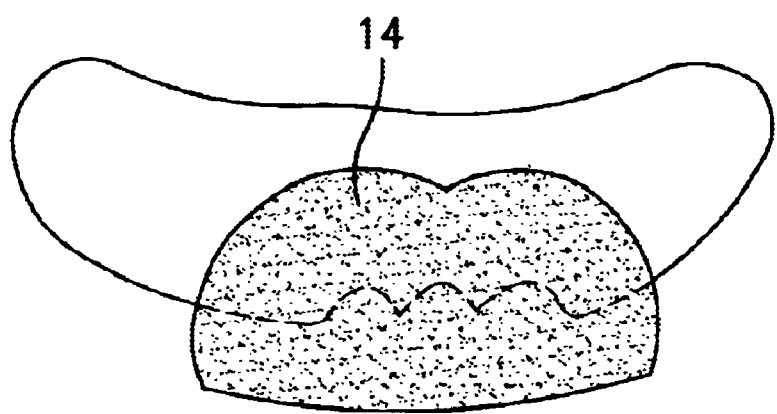
FIG. 2 is an elevational view of the dental arch with putty material positioned thereon.
Figure 3:
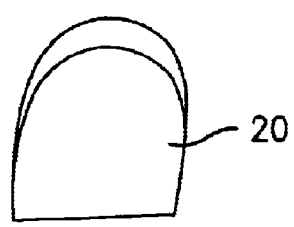
FIG. 3 is an elevational view of a porcelain-fused-to-metal crown.
Figure 4:
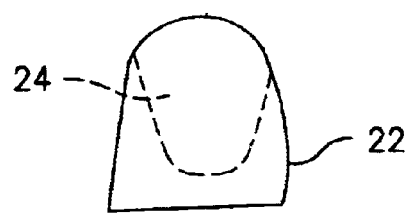
FIG. 4 is an elevational view of an all-ceramic crown.
Figure 5:
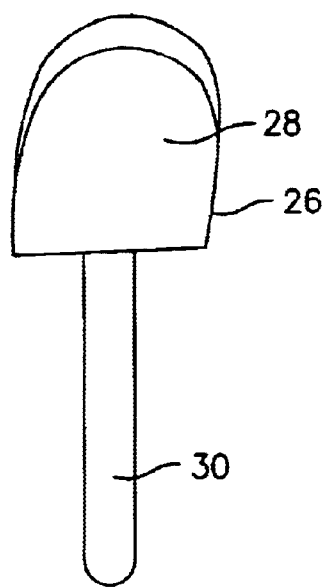
FIG. 5 is an elevational view of a shade guide component.
Figure 6:
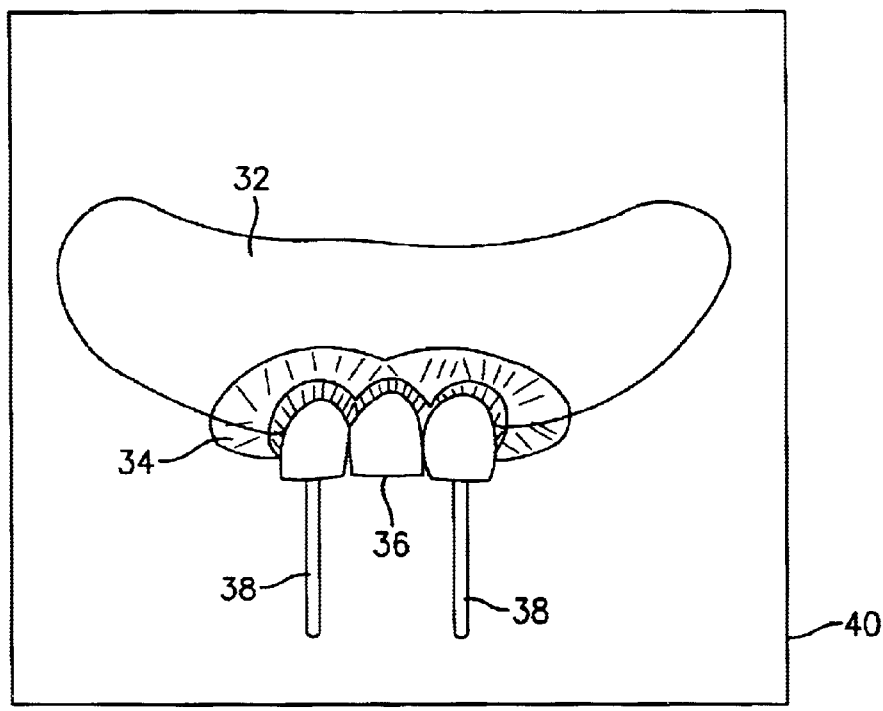
FIG. 6 is an elevational view of the mouth simulator apparatus herein.
Figure 7:
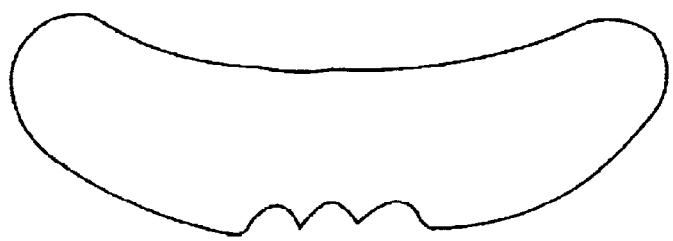
FIG. 7 is a facial view of a dental arch of the mouth simulator apparatus herein.
Figure 8:
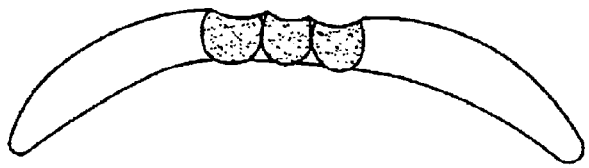
FIG. 8 is an incisal view of a dental arch of the mouth simulator apparatus herein.

Reference is hereby made to the Figures wherein FIG. 1 shows a dental arch 10. Dental arch 10 may include mechanical retentive features such as grooves, holes, nodules, beads or the like, on the surface for retaining a putty material thereon. Retentive holes 12 are shown in FIG. 1 located over a main portion of dental arch 10 to retain a putty material 14 thereon as shown in FIG. 2. FIG. 3 depicts a porcelain-fused-to-metal crown 20 and FIG. 4 depicts an all-ceramic crown 22 wherein some tooth colored composite material 24 is inserted under crown 22 to simulate an underlying tooth or stump. FIG. 5 shows a shade guide component 26 having a tooth-shaped section 28 and a rod or stick 30 extending therefrom. FIG. 6 depicts a mouth simulator apparatus 30 having a dental arch 32 with putty material 34 adhered thereto and contoured to form a papillae. A newly fabricated crown 36 is inserted onto putty material 34 in order to determine if the shade thereof is accurate. Shade guide components 38 are inserted on each side of crown 36 to compare the shade of crown 36 to components 38. The mouth simulator apparatus is not limited to single crowns and may be used for any dental restorative material which must be shaded to accurately match the shade of teeth in a person's mouth including but not limited to orthodontic appliances, bridges, space maintainers, tooth replacement appliances, splints, crowns, partial crowns, dentures, posts, artificial teeth, jackets, inlays, onlays, facings, veneers, facets, implants, abutments, cylinders, and connectors. The apparatus may further include a background material 40 to simulate the oral environment. FIG. 7 is directed to a facial view of a dental arch and FIG. 8 is directed to an incisal view of a dental arch.

The mouth simulator apparatus is further useful for anyone attempting to establish a spectrophotometer shade guide standard for his porcelain or composite system or product line. It is necessary for the spectral camera to see the custom shade guide in the same surroundings as natural teeth in order to produce correlating spectral data.

This mouth simulator apparatus is helpful for general use in dental laboratories and dental offices, as well as manufacturing facilities, for the purpose of viewing and evaluating composite and ceramic restorations when compared to commercially available or custom-designed shade guides or other designated custom standards for the quality control of prepared crowns and bridges. Hue, chroma, and value accuracy are more readily observed in this intraoral simulation.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A method for analyzing the shade of a dental restoration comprising:
   providing an apparatus for simulating the oral environment of a person's mouth wherein the apparatus comprises a dental arch; and a putty material positioned on the dental arch for temporarily attaching dental restorations and shade guide components thereto, whereby the putty material is a pink or brown color that closely matches a shade in the person's mouth;
   inserting a restoration in the putty material;
   inserting the one or more shade components proximate the restoration to compare the shade of the restoration with the shade of the shade guide components.

2. The method of claim 1 wherein the one or more shade guide components are selected from the group consisting of commercially available shade guide components, custom-made shade guide components, and shade guide components in the form of denture teeth.

3. The method of claim 1 wherein the apparatus further comprises a background material for simulating the oral material for simulating the oral environment.

4. The apparatus of claim 1 wherein the dental restoration is selected from the group consisting of orthodontic appliances, bridges, space maintainers, tooth replacement appliances, splints, crowns, partial crowns, dentures, posts, artificial teeth, jackets, inlays, onlays, facings, veneers, facets, implants, abutments, cylinders, and connectors.

* * * * *

UNITED STATES PATENT AND TRADEMARK OFFICE
CERTIFICATE OF CORRECTION

PATENT NO.   : 6,623,271 B2
DATED        : September 23, 2003
INVENTOR(S)  : Jana N. Pruden It is certified that error appears in the above-identified patent and that said Letters Patent is hereby corrected as shown below:

Column 4,
Line 65, after "inserting" delete "the" and after "shade" insert -- guide --
Line 67, before "shade guide" insert -- one or more --

Column 5,
Line 7, after "simulating" delete "the oral material for simulating"

Column 6,
Line 1, after "The" delete "apparatus" and insert -- method --

Signed and Sealed this

Thirteenth Day of January, 2004

JON W. DUDAS
*Acting Director of the United States Patent and Trademark Office*